United States Patent
Madhyastha

(10) Patent No.: US 7,314,857 B2
(45) Date of Patent: Jan. 1, 2008

(54) SYNERGISTIC ANTIMICROBIAL COMPOSITIONS AND METHODS OF INHIBITING BIOFILM FORMATION

(75) Inventor: Srinivasa Madhyastha, Winnipeg (CA)

(73) Assignee: Kane Biotech Inc., Winnipeg, Manitoba (CA)

( * ) Notice: Subject to any disclaimer, the term of this patent is extended or adjusted under 35 U.S.C. 154(b) by 210 days.

(21) Appl. No.: 10/781,464

(22) Filed: Feb. 17, 2004

(65) Prior Publication Data

US 2005/0049181 A1 Mar. 3, 2005

Related U.S. Application Data

(60) Provisional application No. 60/497,337, filed on Aug. 25, 2003.

(30) Foreign Application Priority Data

Dec. 4, 2003 (CA) .................................. 2452032

(51) Int. Cl.
*A61K 38/16* (2006.01)
*C07K 14/195* (2006.01)

(52) U.S. Cl. ............ 514/2; 514/6; 514/8; 514/12; 530/350; 530/400; 435/4; 435/252.1; 435/252.33

(58) Field of Classification Search ............ 514/2, 514/6, 8, 12; 530/400, 350; 435/4, 252.33, 435/253.3, 252.1
See application file for complete search history.

(56) References Cited

U.S. PATENT DOCUMENTS

| | | | |
|---|---|---|---|
| 5,688,516 A | 11/1997 | Raad et al. | |
| 6,267,979 B1 | 7/2001 | Raad et al. | |
| 2002/0001582 A1* | 1/2002 | Charter et al. | 424/94.6 |
| 2002/0141986 A1 | 10/2002 | Lim et al. | |
| 2003/0148399 A1* | 8/2003 | Nemori et al. | 435/7.4 |

FOREIGN PATENT DOCUMENTS

| | | | |
|---|---|---|---|
| CA | 2284364 | | 4/2000 |
| EP | 0629347 A1 | * | 12/1994 |
| WO | WO 96/06532 | * | 3/1996 |

OTHER PUBLICATIONS

Leitch et al. , Current Eye Research 19, 12-9 (Jul. 1999).*
Ellison et al., J. Clin. Invest. 88, 1080-1091 (1991).*
Johnson, Egg Uses and Processing Technologies (1994), 177-191, edited by J. S. Sim & S. Nakai.*
Darouiche, R. et al., "Antimicrobial activity and durability of a novel antimicrobial-impregnated bladder catheter," *International Journal of Antimicrobial Agents*, vol. 8, Issue 4, pp. 243-247—Abstract only (May 1997).
Schierholz J. et al., "Controlled release of antibiotics from biomedical polyurethanes morphological and structural features," *Biomaterials*, vol. 18, No. 12, pp. 839-844—Abstract only (Jun. 1997).
Tunney, M. et al., "Infection associated with medical devices," *Reviews in Medical Microbiology*, vol. 7, No. 4, pp. 195-205 (1996).
Bezkorovainy, A., "Antimicrobial properties of iron-binding proteins," *Adv. Exp. Med. Biol.*, vol. 135, pp. 139-154, Abstract only (1981).
Costerton, J. et al., "Bacterial Biofilms: A Common Cause of Persistent Infections," *Science*, vol. 284, pp. 1318-1322 (May 21, 1999).
Darouiche, R. et al., "A comparison of two antimicrobial-impregnated central venous catheters. Catheter Study Group," *N. Engl. J. Med.*, vol. 340, No. 1, pp. 1-8, Abstract only (2 pages) (Jan. 7, 1999).
Darouiche, R. et al., "Antimicrobial activity of antiseptic-coated orthopaedic devices," *Int. J. Antimicrob. Agents*, vol. 10, No. 1, pp. 83-86, Abstract only (Apr. 1998).
Donlan, R., "Biofilms and Device-Associated Infections," *Emerging Infectious Diseases*, vol. 7, No. 2, pp. 277-281 (Mar.-Apr. 2001).
Fallgren, C. et al., "In vitro anti-staphylococcal activity of heparinized biomaterials bonded with combinations of rifampicin," *Zentralbl Bakteriol*, vol. 287, No. 1-2, pp. 19-31, Abstract only (2 pages) (Jan. 1998).
Jackson, D. et al., "Biofilm Formation and Dispersal under the Influence of the Global Regulator CsrA of *Escherichia coli*," *J. of Bacteriology*, vol. 184, No. 1, pp. 290-301 (Jan. 2002).
Johnson, J. et al., "Activities of a Nitrofurazone-Containing Urinary Catheter and a Silver Hydrogel Catheter against Multidrug-Resistant Bacteria Characteristic of Catheter-Associated Urinary Tract Infection," *Antimicrobial Agents and Chemotherapy*, vol. 43, No. 12, pp. 2990-2995 (Dec. 1999).

(Continued)

*Primary Examiner*—Chih-Min Kam
(74) *Attorney, Agent, or Firm*—Merchant & Gould P.C.

(57) ABSTRACT

A synergistic antimicrobial composition for inhibiting biofilm formation includes an iron-sequestering glycoprotein, a cationic polypeptide and a chelating agent, or an iron-sequestering glycoprotein and a chelating agent, or an iron-sequestering glycoprotein and a cationic polypeptide. Additionally, surfactants and quaternary ammonium compounds may also be advantageously combined with iron-sequestering glycoproteins in an antimicrobial composition. Methods of using a synergistic composition for inhibiting medical device biofilm formation are also disclosed.

11 Claims, 13 Drawing Sheets

OTHER PUBLICATIONS

Jones, D. et al., "Physicochemical characterization of hexetidine-impregnated endotracheal tube poly(vinyl chloride) and resistance to adherence of respiratory bacterial pathogens," *Pharm. Res.*, vol. 19, No. 6, pp. 818-824, Abstract only (Jun. 2002).

Maki, D. et al., "Engineering Out the Risk of Infection with Urinary Catheters," *Emerging Infectious Diseases*, vol. 7, No. 2, pp. 1-6 (Mar.-Apr. 2001).

Petrillo, V. et al., "A Case Report of Vascular Catheter-Associated Bacteremia caused by *Mycobacterium tuberculosis* in a Non-Immunosuppressed Patient," *Rev. Inst. Med. trop. S. Paulo*, vol. 41, No. 3, pp. 203-204 (May-Jun. 1999).

Raad, I. et al., "Minocycline and ethylenediaminetetraacetate for the prevention of recurrent vascular catheter infections," *Clin. Infect. Dis.*, vol. 25, No. 1, pp. 149-151, Abstract only (Jul. 1997).

Raad, I. et al., "Antimicrobial durability and rare ultrastructural colonization of indwelling central catheters coated with minocycline and rifampin," *Crit. Care Med.*, vol. 26, No. 2, pp. 219-224, Abstract only (2 pages) (Feb. 1998).

Schieroholz, J. et al., "The antimicrobial efficacy of a new central venous catheter with long-term broad-spectrum activity," *J. of Antimicrobial Chemotherapy*, vol. 46, pp. 45-50 (2000).

Strickler, D., "Biomaterials to prevent nosocomial infections: is silver the gold standard?" *Curr. Opin. Infect. Dis.*, vol. 13, No. 4, pp. 389-393, Abstract only (Aug. 2000).

Valenti et al., "Studies of the antimicrobial activity of ovotransferrin", *Int. J. Tissue React.* 5: 97-105 (1983) (abstract only).

International Preliminary Report on Patentability dated Feb. 27, 2006.

* cited by examiner

SYNERGISTIC ANTIMICROBIAL COMPOSITIONS AND METHODS OF INHIBITING BIOFILM FORMATION

CROSS-REFERENCE TO RELATED APPLICATIONS

This application claims priority under 35 U.S.C. § 119(e) to U.S. provisional application No. 60/497,337, filed Aug. 25, 2003 and priority under 35 U.S.C. § 119(b) to Canadian patent application number 2,452,032 filed Dec. 4, 2003 the disclosures of which are hereby incorporated by reference.

FIELD OF THE INVENTION

This invention relates to synergistic antimicrobial compositions which inhibit biofilm formation on or in medical devices such as catheters as well as other devices.

BACKGROUND OF THE INVENTION

Biofilms are medically and industrially important because they can accumulate on a wide variety of substrates and are resistant to antimicrobial agents and detergents. Microbial biofilms develop when microorganisms irreversibly adhere to a surface and produce extracellular polymers that facilitate adhesion and provide a structural matrix. Therefore inhibiting adhesion to surfaces is important. This surface may be inert, non-living material or living tissue.

Biofilm-associated microorganisms behave differently from planktonic (freely suspended) organisms with respect to growth rates and ability to resist antimicrobial treatments and therefore pose a public health problem. Many chronic infections that are difficult or impossible to eliminate with conventional antibiotic therapies are known to involve biofilms. A partial list of the infections that involve biofilms includes: otitis media, prostatitis, vascular endocarditis, cystic fibrosis pneumonia, meliodosis, necrotising faciitis, osteomyelitis, peridontitis, biliary tract infection, struvite kidney stone and host of nosocomial infections (Costerton, J. W., et al., Science, 284:1318-1322, 1999).

Biofilms on indwelling medical devices may be composed of gram-positive or gram-negative bacteria or yeasts. Bacteria commonly isolated from these devices include the gram-positive *Enterococcus faecalis* (*E. faecalis*), *Staphylococcus epidermidis* (*S. epidermidis*), *Staphylococcus aureus* (*S. aureus*), *Streptococcus viridans* (*St. viridans*); and the gram-negative *Escherichia coli* (*E.coli*), *Klebsiella pneumoniae* (*K. pneumoniae*), *Proteus mirabilis* (*P. mirabilis*) and *Pseudomonas aeruginosa* (*P. aeruginosa*)(Donlan, R. M., Emerging Infectious Diseases, 7:277-281, 2001). The organisms most commonly isolated from urinary catheter biofilms are *Staphylococcus epidermidis, Enterococcus faecalis, E. coli, Proteus mirabilis, Pseudomonas aeruginosa* and *Klebsiella pneumoniae*. Urinary catheters and central venous catheters are notorious examples of infection prone devices. Catheter-associated urinary tract infection is the most common nosocomial infection. Each year, more than 1 million patients in US hospitals acquire such an infection. Catheter-associated urinary tract infection is the second most common cause of nosocomial infections (Maki, D. G. and P. A. Tambyah., Emerging Infectious Diseases, 7:1-6, 2001).

In recent years, there have been numerous efforts to sequester antimicrobials and antibiotics on the surface of or within devices that are then placed in the vasculature or urinary tract as a means of reducing the incidence of device-related infections. These antimicrobial agents are of varying chemical composition and can include chelating agents (EDTA, EGTA, DTPA, etc.), cationic polypeptides (protamine, polylysine, lysozyme, etc.), surfactants (SDS, Tween-80, surfactin, etc.), quaternary ammonium compounds (benzalkonium chloride, tridodecyl methyl ammonium chloride, didecyl dimethyl ammonium chloride, etc.). The iron-sequestering glycoproteins such as lactoferrin from milk and ovotransferrin (conalbumin) from egg white are iron-binding glycoproteins, which inhibit the growth of certain bacteria by making iron unavailable for bacterial metabolism (Bezkorovainy, A., Adv. Exp. Med. Biol. 135: 139-154, 1981).

The main methods of antimicrobial catheter preparation include immersion or flushing, coating, drug-polymer conjugate and impregnating (Tunny, M. M., et al., Rev. Med. Microbiol., 74: 195-205, 1996). In a clinical setting, suitable catheters can be treated by immersion immediately prior to placement, which offers flexibility and control to clinicians in certain situations. Several studies have examined the clinical efficacy of catheters coated with antimicrobial agents. Polyurethane catheters coated with minocycline and EDTA showed potential in reducing recurrent vascular catheter-related infections (Raad, I. I. et al., Clinical Infectious Diseases, 25: 149-151, 1997). Minocycline and rifampin coatings have been shown to significantly reduce the risk of catheter-associated infections (Raad, I. I. et al., Crit. Care Med., 26: 219-224, 1998). Minocycline coated onto urethral catheters has been shown to provide some protection against colonization (Darouiche, R. O., et al., Int. J. Antimicrob. Ag. 8: 243-247,1997). Johnson, et al., described substantial in vitro antimicrobial activity of a commercially available nitrofurazone coated silicone catheter (Johnson, J. R., et al., Antimicrob. Agents. Chemother. 43: 2,990-2,995,1999). The antibacterial activity of silver-containing compounds as antimicrobial coatings for medical devices has been widely investigated. Silver-sulfadiazine used in combination with chlorhexidine has received particular interest as a central venous catheter coating (Stickler, D. J., Curr. Opin. Infect. Dis., 13:389-393, 2000; Darouiche, R. O., et al., New Eng. J. Med., 340: 1-8,1999). The loading of antimicrobial agents into medical devices by immersion or coating technologies has the advantage of being relatively simple. However, the limited mass of drug that can be incorporated may be insufficient for a prolonged antimicrobial effect, and the release of the drug following clinical insertion of the device is rapid and relatively uncontrolled. A means of reducing these problems is by direct incorporation of the antimicrobial agent into the polymeric matrix of the medical device at the polymer synthesis stage or at the device manufacture stage. Rifampicin has been incorporated into silicone in an attempt to prevent infection of cerebrospinal fluid shunts with some success (Schierholz, J. M., et al., Biomaterials, 18: 839-844,1997), and hexetidine in PVC was observed to decrease bacterial colonization (Jones, D. S., et al., Pharm. Res., in press). Iodine has also been incorporated into medical device biomaterials. Coronary stents have been modified to have antithrombogenic and antibacterial activity by covalent attachment of heparin to silicone with subsequent entrapment of antibiotics in cross-linked collagen bound to the heparinised surface (Fallgren, C., et al., Zent-.Fur Bakt.-Int. J. Med. Micro. Vir., Paraotol. Infect. Dis., 287:19-31,1998).

Charter, E. A., et al., disclosed a composition consisting of avidin, ovotransferrin, chicken immunoglobulins, chitosan, polylysine, protamine, nisin, EDTA, rosemary, cinnemaldehyde, allicin and eugenol for inhibiting the growth of microoraganisms on fruit, vegetable, turfgrass and other plant systems by the application of specific enzymes either alone or in combination with fungicidally active agents (U.S. patent application Ser. No. 20020001582, 2002). In U.S. Pat. No. 5,363,754 (2001), Welle, C. J., et al., disclosed the method of preparing a kit for flushing a medical device. The kit includes a solution containing an antibiotic, an anticoagulant (protamine sulfate) and an antithrombotic agent or chelating agent useful for preventing infections caused by bacterial growth in catheters. Budny, J. A. et al., discloses various antimicrobial agents for anchoring to biofilms (U.S. patent application Ser. No. 20020037260, 2002). Raad, et al., in U.S. Pat. No. 5,362,754 (1994) disclosed that pharmaceutical compositions of a mixture of minocycline and EDTA were useful in maintaining the patency of a catheter port. Recently, Raad, I. and R. Sheretz in U.S. Pat. No. 5,688,516 (1997) further disclosed that effective catheter flush solutions could be prepared with non-glycopeptide antimicrobial agent, an antithrombic agent, an anticoagulant and a chelating agent selected from the group consisting of EDTA, EGTA and DTPA. U.S. Pat. No. 6,187,768 to Welle et al. teaches the use of several anticoagulants for use in medical devices, including protamine sulfate. U.S. Pat. No. 6,174,537 to Khan teaches the flushing of intravascular catheters using EDTA in combination with salts of sodium, calcium and lactic acid.

The methods currently in use for prevention of biofilms act at the level of removal versus formation of the biofilms. These methods are costly, often involve the use of caustic chemicals, and often provide only short-term prevention. In medical devices, various techniques have been described that incorporate potentially toxic metal ions in the form of metal salts into materials that make up the medical devices. The protection against biofilm formation lasts only as long as the coating remains on the device. A method of long-term prevention from biofilm formation that acts at the level of prevention of biofilm formation is needed. Also needed is a composition that allows for low quantities of the composition to be used effectively, thus reducing toxicity or other side effects to the user or patient without sacrificing effectiveness against biofilm formation. There is also a need for antimicrobial compositions that are environmentally friendly, medically acceptable, highly effective and relatively economical to manufacture on a commercial scale for preventing biofilm formation in biomedical devices.

SUMMARY OF THE INVENTION

Accordingly, one aspect of the invention provides a composition comprising: (a) a small amount of at least one iron-sequestering glycoprotein; and (b) a sparing amount of at least one cationic polypeptide, wherein the amount of each components (a) and (b) is sufficient to form, in combination, a synergistic, antimicrobial composition. In yet another alternative embodiment, a composition of the invention comprises: (a) a small amount of at least one iron-sequestering glycoprotein and (b) a sparing amount of at least one chelating agent, wherein the amount of each of components (a) and (b) is sufficient to form, in combination, a synergistic antimicrobial composition. In yet another alternative embodiment, a composition of the invention comprises: (a) a small amount of at least one iron-sequestering glycoprotein, (b) a sparing amount of at least one cationic polypeptide and (c) a sparing amount of at least one chelating agent, wherein the amount of each of components (a), (b) and (c) is sufficient to form, in combination, a synergistic antimicrobial composition.

Thus, the invention provides a composition for inhibiting bacterial biofilm on devices comprising: an iron-sequestering glycoprotein; a cationic polypeptide; and a chelating agent. The composition is effective against biofilms produced by bacterial species selected from the group consisting of *Klebsiella pneumoniae, Pseudomonas aeruginosa* and *Staphylococcus epidermidis*. The composition is effective against biofilms produced by gram-negative bacterial species selected from the group consisting of *Escherichia coli, Proteus mirabilis, Klebsiella pneumoniae* and *Pseudomonas aeruginosa*. The composition is effective against biofilms produced by gram-positive bacterial species selected from the group consisting of *Enterococcus faecalis* and *Staphylococcus epidermidis*.

The invention also provides a composition for inhibiting bacterial biofilm on devices comprising an iron-sequestering glycoprotein; and a cationic polypeptide. The composition is effective against biofilms produced by bacterial species selected from the group consisting of *Staphylococcus epidermidis, Enterococcus faecalis, E. coli, Proteus mirabilis, Pseudomonas aeruginosa, Klebsiella pneumoniae, Staphylococcus aureus, Streptococcus viridans, Klebsiella oxytoca, Staphylococcus saprophyticus, Providentia stuartii* and *Serratia marcescens, Klebsiella pneumoniae, Pseudomonas aeruginosa* and *Staphylococcus epidermidis*. The composition is particularly effective against biofilms produced by bacterial species selected from the group consisting of *Escherichia coli, Proteus mirabilis, Klebsiella pneumoniae Pseudomonas aeruginosa* and *Staphylococcus epidermidis*.

The invention further teaches a composition for inhibiting bacterial biofilm on devices comprising: an iron-sequestering glycoprotein; and a chelating agent. The composition is effective against biofilms produced by bacterial species selected from the group consisting of *Staphylococcus epidermidis, Enterococcus faecalis, E. coli, Proteus mirabilis, Pseudomonas aeruginosa, Klebsiella pneumoniae, Staphylococcus aureus, Streptococcus viridans, Klebsiella oxytoca, Staphylococcus saprophyticus, Providentia stuartii* and *Serratia marcescens, Klebsiella pneumoniae, Pseudomonas aeruginosa* and *Staphylococcus epidermidis*. The composition is particularly effective against biofilms produced by *Staphylococcus epidermidis*.

In an embodiment, the iron-sequestering glycoprotein is between about 125 mg/L and about 2000 mg/L of the composition. The cationic polypeptide is between about 12.5 mg/L and about 200 mg/L of the composition. The chelating agent is between about 12.5 mg/L and about 200 mg/L of the composition.

The iron-sequestering glycoprotein may be selected from the group consisting of ovotransferrin, lactoferrin and serotransferrin. The cationic polypeptide may be selected from the group consisting of protamine sulfate, polylysine, defensin, lactoperoxidase and lysozyme. The chelating agent may be selected from the group consisting of EDTA, EGTA, DTPA, EDDHA, IDA, CDTA, HEDTA, HEIDA and NTA. In an embodiment, the iron-sequestering agent is ovotransferrin, the cationic polypeptide is protamine sulfate, and the chelating agent is EDTA. The ovotransferrin may be present as about 2 mg/ml, the protamine sulfate may be present as about 0.2 mg/ml, and the EDTA may be present as about 0.2 mg/ml.

The composition may further comprise one or more ingredients selected from the group consisting of: water, a binding or bonding or coupling agent, a surfactant, a quaternary ammonium compound, an antibiotic and a pH adjuster.

The invention also teaches methods of preparing a device comprising treating at least a surface of the device with the composition of the invention. The invention also teaches methods of preparing a device comprising coating a device with the composition of the invention. The method may further comprise treating the device with quaternary ammonium compound before coating the device with the composition. The quaternary ammonium compound may be selected from the group consisting of tridodecylmethyl ammonium chloride and benzalkonium chloride. The composition may further comprise hydrogel. The hydrogel may be selected from the group consisting of polyvinylpyrrolidone-hydrogel, polyvinyl alcohol-hydrogel and polyethylene glycol-hydrogel.

The treated device may be a medical device. The device may be a catheter. The catheter may be an indwelling catheter. The indwelling catheter may be selected from a group consisting of a central venous catheter, a peripheral intravenous catheter, an arterial catheter, a haemodialysis catheter, an umbilical catheter, precutaneous nontunneled silicone catheter, a cuffed tunneled central venous catheter and a subcutaneous central venous port. The catheter may be selected from a group consisting of urinary catheter and a peritoneal catheter. The device may be selected from the group consisting of catheters, pacemakers, prosthetic heart valves, prosthetic joints, voice prostheses, contact lenses, and intrauterine devices. The device may be selected from the group consisting of pipes, heat exchangers and computer chips.

The invention also teaches methods of preparing a device comprising incorporating the composition of the invention into polymers which are used to form the device, and methods of preparing a device comprising impregnating the composition of the invention into the device.

DETAILED DESCRIPTION OF THE INVENTION

Figure 1:
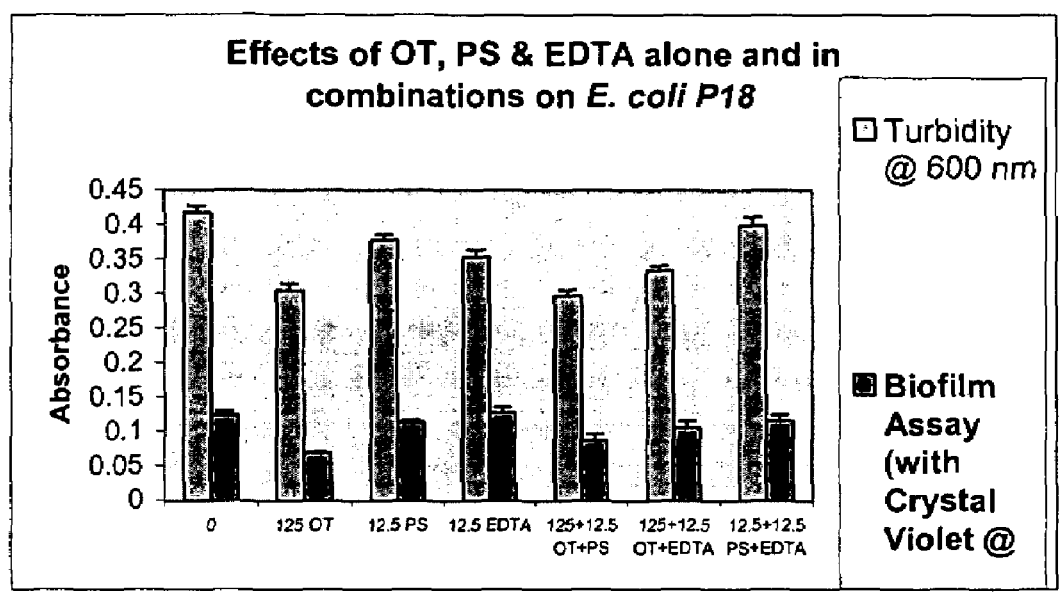
FIG. 1 is a bar graph showing the effects of ovotransferrin (OT), protamine sulfate (PS) and EDTA (ethylenediaminetetraacetate) alone and in combinations (OT+PS, OT+EDTA & PS+EDTA) on biofilm formation by *E. coli*.
Figure 2:
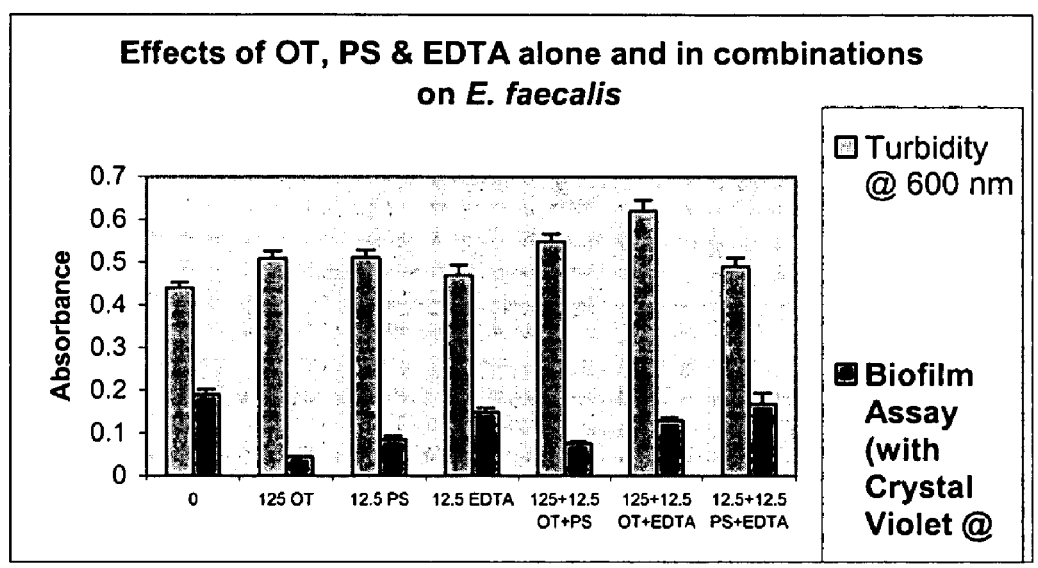
FIG. 2 is a bar graph showing the effects of ovotransferrin (OT), protamine sulfate (PS) and EDTA (ethylenediaminetetraacetate) alone and in combinations (OT+PS, OT+EDTA & PS+EDTA) on biofilm formation by *Enterococcus faecalis*.
Figure 3:
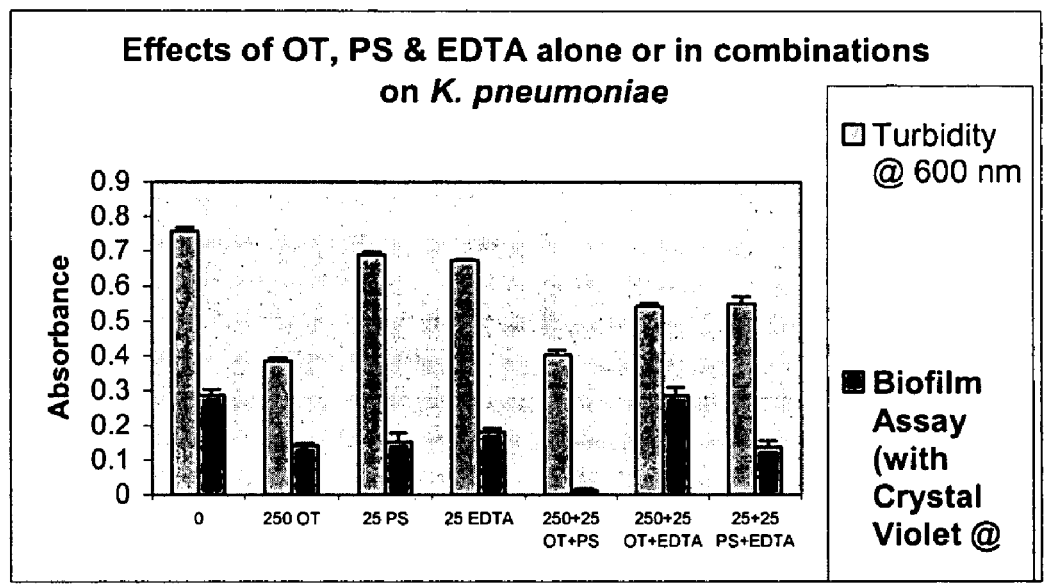
FIG. 3 is a bar graph showing the effects of ovotransferrin (OT), protamine sulfate (PS) and EDTA (ethylenediaminetetraacetate) alone and in combinations (OT+PS, OT+EDTA & PS+EDTA) on biofilm formation by *Klebsiella pneumoniae*.
Figure 4:
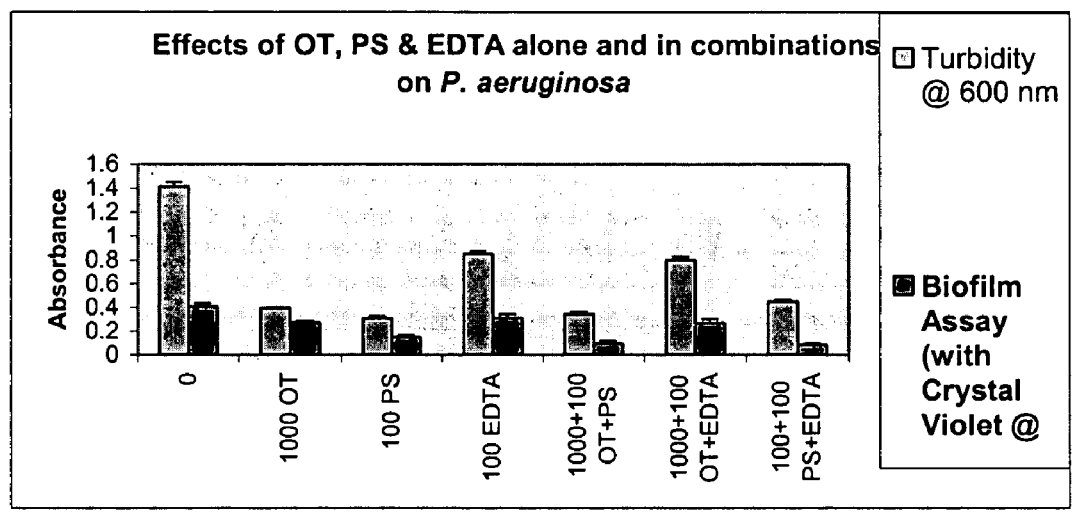
FIG. 4 is a bar graph showing the effects of ovotransferrin (OT), protamine sulfate (PS) and EDTA (ethylenediaminetetraacetate) alone and in combinations (OT+PS, OT+EDTA & PS+EDTA) on biofilm formation by *Pseudomonas aeruginosa*.
Figure 5:
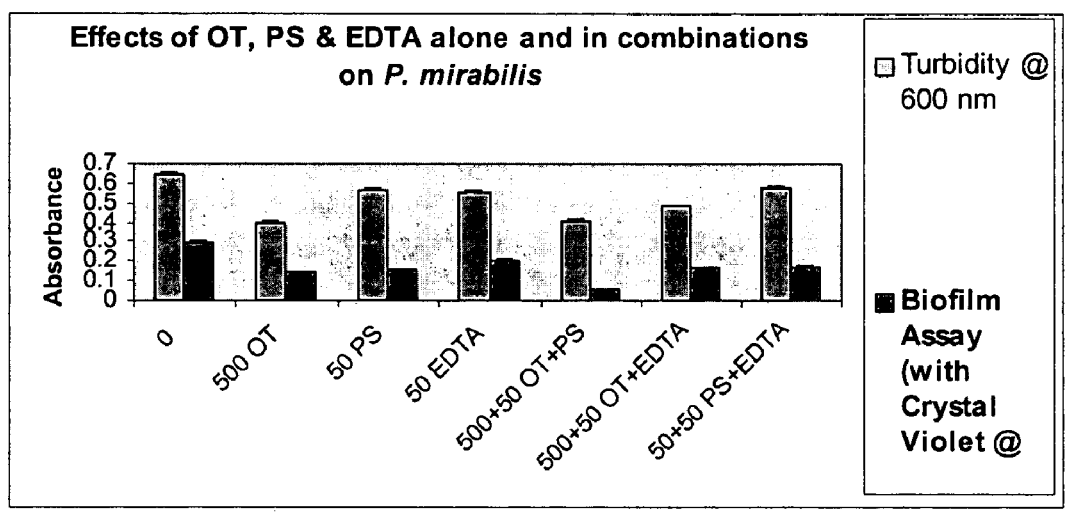
FIG. 5 is a bar graph showing the effects of ovotransferrin (OT), protamine sulfate (PS) and EDTA (ethylenediaminetetraacetate) alone and in combinations (OT+PS, OT+EDTA & PS+EDTA) on biofilm formation by *Proteus mirabilis*.
Figure 6:
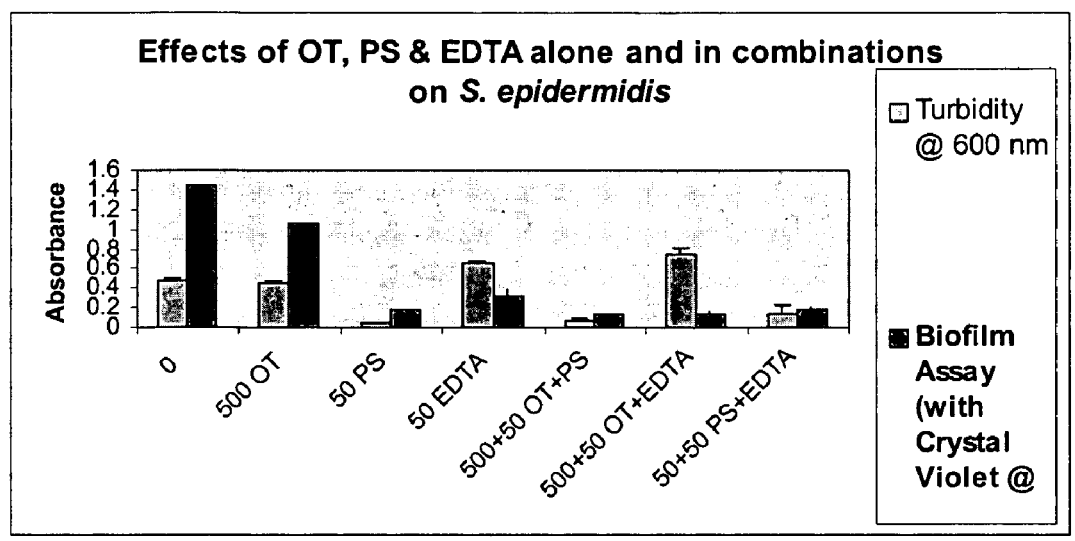
FIG. 6 is a bar graph showing the effects of ovotransferrin (OT), protamine sulfate (PS) and EDTA (ethylenediaminetetraacetate) alone and in combinations (OT+PS, OT+EDTA & PS+EDTA) on biofilm formation by *Staphylococcus epidermidis*.
Figure 7:
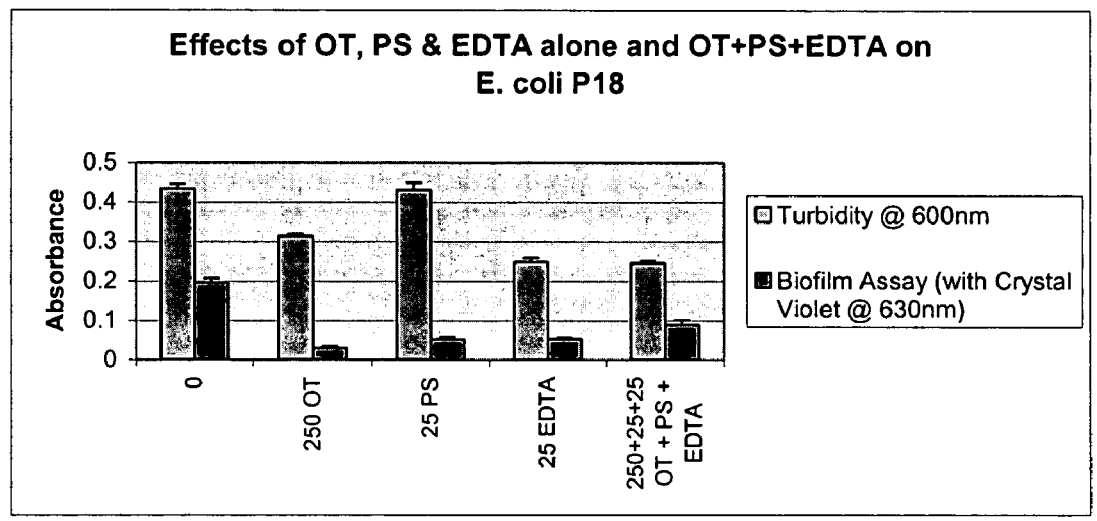
FIG. 7 is a bar graph showing the effects of ovotransferrin (OT), protamine sulfate (PS) and EDTA alone and in combination (OT+PS+EDTA) on biofilm formation by *E. coli*.
Figure 8:
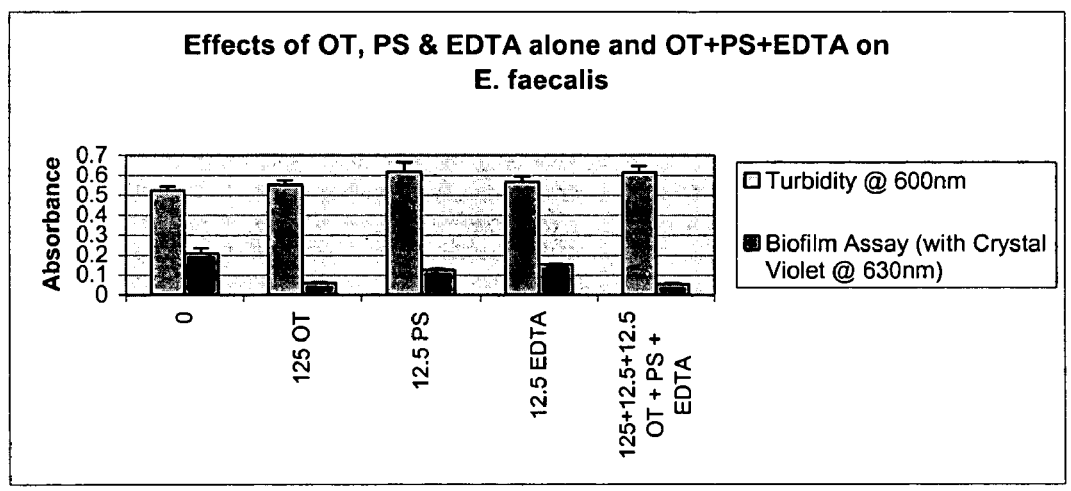
FIG. 8 is a bar graph showing the effects of ovotransferrin (OT), protamine sulfate (PS) and EDTA alone and in combination (OT+PS+EDTA) on biofilm formation by *Enterococcus faecalis*.
Figure 9:
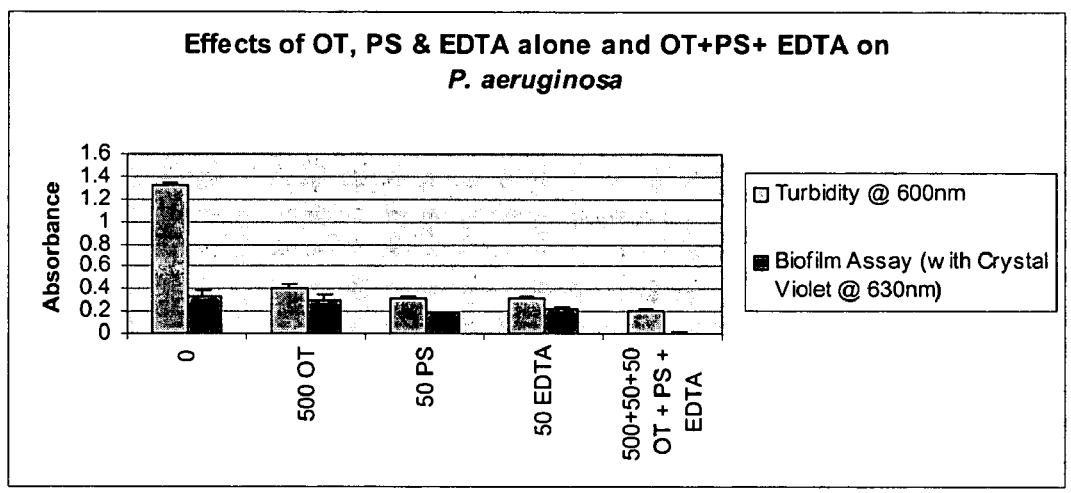
FIG. 9 is a bar graph showing the effects of ovotransferrin (OT), protamine sulfate (PS) and EDTA alone and in combination (OT+PS+EDTA) on biofilm formation by *Pseudomonas aeruginosa*.
Figure 10:
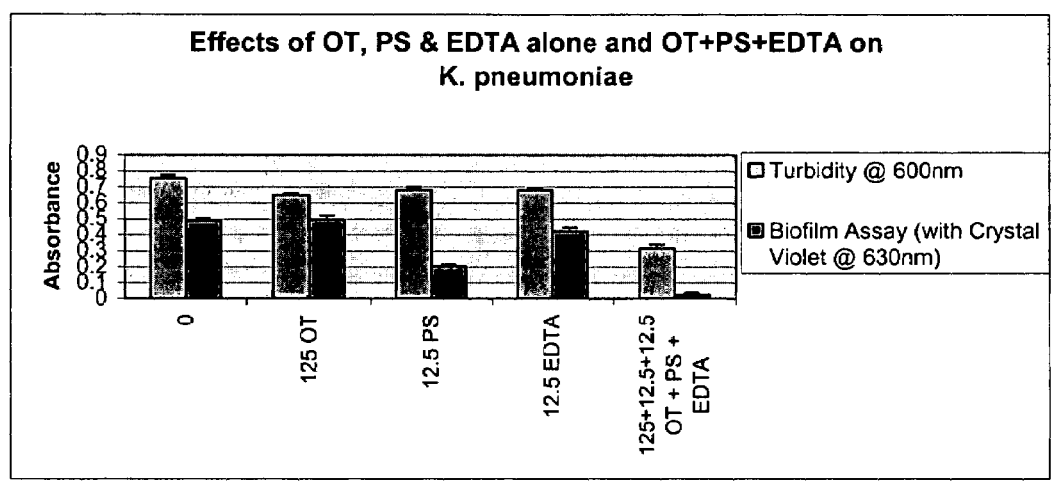
FIG. 10 is a bar graph showing the effects of ovotransferrin (OT), protamine sulfate (PS) and EDTA alone and in combination (OT+PS+EDTA) on biofilm formation by *Klebsiella pneumoniae*.
Figure 11:
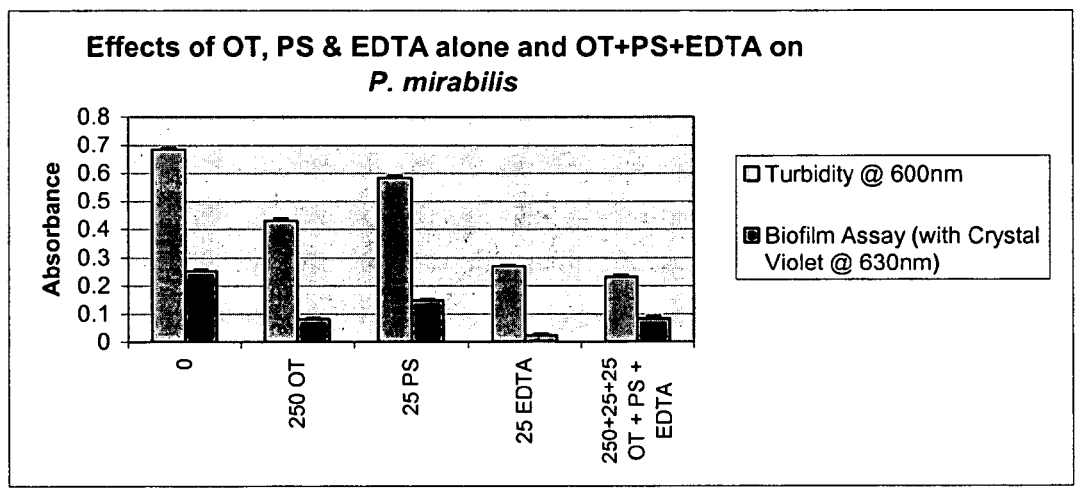
FIG. 11 is a bar graph showing the effects of ovotransferrin (OT), protamine sulfate (PS) and EDTA alone and in combination (OT+PS+EDTA) on biofilm formation by *Proteus mirabilis*.
Figure 12:
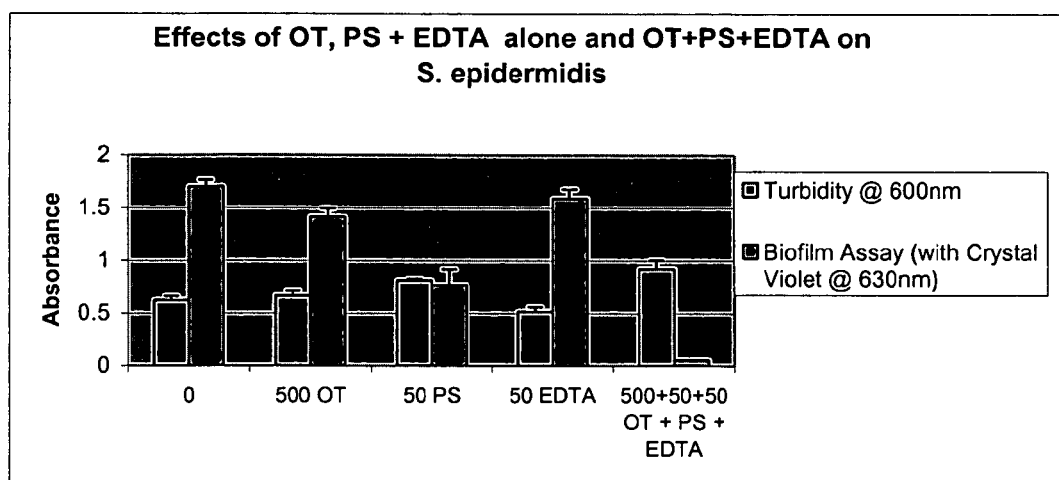
FIG. 12 is a bar graph showing the effects of ovotransferrin (OT), protamine sulfate (PS) and EDTA alone and in combination (OT+PS+EDTA) on biofilm formation by *Staphylococcus epidermidis*.

The present inventor has found that an unexpectedly high level of synergy occurs in antimicrobial compositions that contain at least one iron-sequestering glycoprotein, one cationic polypeptide and one chelating agent. The synergy is evidenced by the small quantities of each of these compounds that need to be used to produce an effective antimicrobial composition. The necessary overall amount of the compounds is less than that which would be required if any of the compounds were to be used on their own. In particular, it is possible to use small amounts of iron-sequestering glycoproteins, which can be expensive but are biologically acceptable, with small amounts of cationic polypeptides, which are also biologically acceptable and small amounts of chelating agents, which are biologically acceptable at lower concentrations and are effective antimicrobials. Synergy was found with antimicrobial compositions that contain at least one iron-sequestering glycoprotein with at least one cationic polypeptide or at least one chelating agent.

The present invention teaches synergistic antimicrobial compositions offering superior anti-biofilm activity, containing combinations of iron-sequestering glycoproteins with other antimicrobial agents, such as, for example, cationic polypeptides and/or chelating agents with quaternary ammonium compounds or surfactants. The invention also teaches the use of synergistic antimicrobial composition in immersing or flushing or coating devices, such as catheters to inhibit biofilm formation. The compositions can also be incorporated into polymers which are used to form the devices such as catheters by impregnating or by drug-polymer conjugation.

The synergistic antimicrobial compositions require remarkably small amounts of active ingredients (compared to that which has been used in the fast) to be effective. Because such small amounts of active ingredients need to be used for these inventive synergistic antimicrobial compositions, the compositions are medically safe and environmentally friendly. These compositions have properties that include those of the separate compounds but go beyond them in efficacy and scope of application. The extremely low levels, and hence increased efficacy, of the active compounds or ingredients make this invention very desirable.

Novel compositions that combine iron-sequestering glycoprotein together with cationic polypeptides and/or chelating agents such that lesser quantities of iron-sequestering glycoprotein, cationic polypeptides and/or chelating agents than would normally be necessary for an antimicrobial composition are used to achieve significant biofilm inhibition. Higher concentrations of these compounds can be used if it is desired for certain applications.

The amount of iron-sequestering glycoprotein to be used in the synergistic antimicrobial composition of this invention can be between 125 to 2000 mg/L. The higher end of this stated range might be used to prepare a concentrated product that would be diluted prior to use. For non-concentrated products, the amount of iron-sequestering glycoprotein to be used in this invention is preferably between about 125 to 1000 mg/L.

The amount of cationic polypeptide to be used should be between about 12.5 to 200 mg/L. The higher end of this range might apply if the compositions were formulated as a concentrate. For non-concentrated products, the amount of cationic polypeptide to be used in this invention is preferably between about 12.5-100 mg/L.

The amount of chelating agent to be used should be between about 12.5 to 200 mg/L. The higher end of this range might apply if the compositions were formulated as a concentrate. For non-concentrated products, the amount of chelating agent to be used in this invention is preferably between about 12.5-100 mg/L.

By one method, if a three-component composition is to be formed containing a chelating agent, a cationic polypeptide and an iron-sequestering glycoprotein, these compounds can be combined in the following manner. With good stirring, a chelating agent can be dissolved in water. A cationic polypeptide can be added thereafter, followed by an iron-sequestering glycoprotein. It should be noted, however, that the addition order is not critical.

Since chelating agent and cationic polypeptide, such as, EDTA (ethylenediaminetetraacetate) and protamine sulfate, respectively are not readily soluble in water, they are preferably added to the composition in small amounts and stirred well. It may be necessary to adjust the pH preferably to 7.4 in order to make EDTA readily soluble.

Also, quaternary ammonium compounds and surfactants also may be advantageously combined with iron-sequestering glycoprotein in an antimicrobial composition. A composition of the invention comprises: (a) a small amount of at least one iron-sequestering glycoprotein; and (b) a sparing amount of at least one compound from the group consisting of a quaternary ammonium compounds and/or a surfactant, wherein, the amount of each of components (a) and (b) is sufficient to form, in combination, a synergistic antimicrobial composition.

The present invention includes adding an effective amount of composition to the surface of an object. This coating prevents the formation of biofilm on the surface, while showing moderate effect on the viability of microbes. The moderate effect on the viability of microbes can be attributed to biologically acceptable non-lethal compounds in the composition, which include iron-sequestering ovotransferrin and protamine sulfate. Lethal compounds such as silver or antibiotics often create selective pressure to increase the likelihood of amplifying silver-resistant or antibiotic resistant strains, thus rendering the antibiofilm agents useless. This is an important consideration when the object to be coated is a medical device that will be implanted in the body, where resident bacteria exist. The apparatus and method of the present invention uses composition to prevent biofilm formation. The effect of composition on biofilm formation by catheter-associated bacterial strains on microtiter plates and on vinyl urethral catheters was investigated.

Examples of bacteria that produce biofilms (biofilm bacteria) which can be inhibited by the present invention include bacteria such as *Staphylococcus epidermidis, Enterococcus faecalis, E. coli, Proteus mirabilis, Pseudomonas aeruginosa, Klebsiella pneumoniae, Staphylococcus aureus*, and *Streptococcus viridans*. These bacteria are commonly found associated with medical devices including catheters. Other bacteria producing biofilms which may be inhibited by the compositions of the present invention include *Klebsiella oxytoca, Staphylococcus saprophyticus, Providentia stuartii* and *Serratia marcescens*.

Examples of devices that can be protected using the compositions of the invention include tubings and other medical devices, such as catheters, pacemakers, prosthetic heart valves, prosthetic joints, voice prostheses, contact lenses, intrauterine devices. Medical devices include disposable or permanent catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field. Medical devices also include any device which may be inserted or implanted into a human being or other animal, or placed at the insertion or implantation site such as the skin near the insertion or implantation site, and which include at least one surface which is susceptible to colonization by biofilm embedded microorganisms. In one specific embodiment, the composition of the invention is integrated into an adhesive, such as tape, thereby providing an adhesive which may prevent growth or proliferation of biofilm embedded microorganisms on at least one surface of the adhesive. Medical devices for the present invention include surfaces of equipment in operating rooms, emergency rooms, hospital rooms, clinics, and bathrooms.

Implantable medical devices include orthopedic implants which may be inspected for contamination or infection by biofilm embedded microorganisms using endoscopy. Insertable medical devices include catheters and shunts which can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex (polytetrafluoroethylene), Dacron™ (polyethylene tetraphthalate), Teflon (polytetrafluoroethylene), latex, elastomers and Dacron™ sealed with gelatin, collagen or albumin, and derivatives or combinations thereof. The medical devices include at least one surface for applying the composition of the invention. Preferably, the composition of the invention is applied to the entire medical device.

The composition of the invention may include any number of active components and base materials known to persons skilled in the art.

While the active components discussed herein may be 100% of the composition of the invention, preferably, the composition contains from at least about 0.01% to about 60% of the active components by weight based upon the total weight of the composition of the invention being employed. In the preferred embodiment, the composition includes from at least about 0.5% to about 30% (by weight) active components.

Other possible components of the composition include, but are not limited to, buffer solutions, phosphate buffered saline, saline, water, polyvinyl, polyethylene, polyurethane, polypropylene, silicone (e.g., silicone elastomers and silicone adhesives), polycarboxylic acids, (e.g., polyacrylic acid, polymethacrylic acid, polymaleic acid, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylamine, polylysine, poly-(dialkylamineoethyl methacrylate), poly-(dialkylaminomethyl styrene) or poly-(vinylpyridine)), polyammonium ions (e.g., poly-(2-methacryloxyethyl trialkyl ammonium ion), poly-(vinylbenzyl trialkyl ammonium ions), poly-(N.N.-alkylypyridinium ion) or poly-(dialkyloctamethylene ammonium ion) and polysulfonates (e.g. poly-(vinyl sulfonate) or poly-(styrene sulfonate)), collodion, nylon, rubber, plastic, polyesters, Gortex (polytetrafluoroethylene), Dacron™ (polyethylene tetraphthalate), Teflon polytetrafluoroethylene), latex, and derivatives thereof, elastomers and Dacron (sealed with gelatin, collagen or albumin, cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the active components and adhesion of the biofilm penetrating coating to at least one surface of the medical device. Linear copolymers, cross-linked copolymers, graft polymers, and block polymers, containing monomers as constituents of the above exemplified polymers may also be used.

The term "effective" is herein defined as a sufficient amount of the active components to substantially prevent the growth or proliferation of biofilm embedded microorganisms on the at least one surface of the medical device in the case of the composition of the invention being a coating; and as a sufficient amount of the active components to substantially penetrate, or break-up, the biofilm on the at least one surface of the medical device, thereby facilitating access of the active components, antimicrobial agents, and/or antifungal agents to the microorganisms embedded in the biofilm, and thus, removal of substantially all of the microorganisms from at least one surface of the medical device in the case of the composition of the invention being a solution. The amount will vary for each of the active components and upon known factors such as pharmaceutical characteristics; the type of medical device; the degree of biofilm embedded microorganism contamination; and the use and length of use.

In another aspect, the invention is directed to a method for coating a medical device. Broadly, the method for coating a medical device includes the steps of providing a medical device, providing, or forming, a composition coating, and applying the composition coating to at least one surface of the medical device in an amount sufficient to substantially prevent the growth or proliferation of biofilm embedded microorganisms on at least one surface of the medical device.

In one specific embodiment, the method for coating a medical device includes the steps of forming a composition of the invention of an effective concentration for activating the active components, and thus substantially preventing the growth or proliferation of microorganisms on at least one surface of the medical device, wherein the composition of the invention is formed by combining a active components and a base material. At least one surface of the medical device is then contacted with the composition of the invention under conditions wherein the composition of the invention covers at least one surface of the medical device. "Contacting" includes, but is not limited to, impregnating, compounding, mixing, integrating, coating, spraying and dipping.

In another aspect the invention relates to a method for inhibiting biofilm embedded microorganisms from at least one surface of the medical device. In one specific embodiment, the method of inhibiting biofilm from at least one surface of the medical device includes the steps of providing a medical device having at least one surface, the at least one surface having biofilm attached thereto, and contacting the medical device with a composition as described in greater detail above. "Contacting" further includes, but is not limited to, soaking, rinsing, flushing, submerging, and washing. The medical device should be contacted with the composition for a period of time sufficient to remove substantially all of the biofilm from the at least one surface of the medical device. In one specific embodiment, the medical device is submerged in the composition for at least 5 minutes. Alternatively, the medical device may be flushed with the composition. In the case of the medical device being a tubing, such as dental drain tubing, the composition may be poured into the dental drain tubing and both ends of the tubing clamped such that the composition is retained within the lumen of the tubing. The tubing is then allowed to remain filled with the composition for a period of time sufficient to remove substantially all of the microorganisms from at least one surface of the medical device, generally, for at least about 1 minute to about 48 hours. Alternatively, the tubing may be flushed by pouring the composition into the lumen of the tubing for an amount of time sufficient to prevent substantially all biofilm growth.

The concentration of active components in the compositions may vary as desired or necessary to decrease the amount of time the composition of the invention is in contact with the medical device. These variations in active components concentration are easily determined by persons skilled in the art.

In specific embodiments of the method for coating devices and the methods for inhibiting biofilm on at least one surface of the medical devices, the step of forming a composition of the invention may also include any one or all of the steps of adding an organic solvent, a medical device material penetrating agent, or adding an alkalinizing agent to the composition, to enhance the reactivity of the surface of the medical device with the composition. In the case of the method for coating medical devices, the organic solvent, medical device material penetrating agent, and/or alkalinizing agent preferably facilitate adhesion of the composition to at least one surface of the medical device.

In another embodiment of the method for coating a medical device, the composition coating is preferably formed by combining a active components and a base material at room temperature and mixing the composition for a time sufficient to evenly disperse the active agents in the composition prior to applying the composition to a surface of the device. The medical device may be contacted with the composition for a period of time sufficient for the composition to adhere to at least one surface of the device. After the composition is applied to a surface of the device, it is allowed to dry.

The device is preferably placed in contact with the composition by dipping the medical device in the composition for a period of time ranging from about 5 seconds to about 120 minutes at a temperature ranging from about 25° C. to about 80° C. Preferably, the device is placed in contact with the composition by dipping the medical device in the composition for about 60 minutes at a temperature of about 45° C. The device is then removed from the composition and the composition is allowed to dry. The medical device may be placed in an oven, or other heated environment for a period of time sufficient for the composition to dry.

Although one layer, or coating, of the composition is believed to provide the desired composition coating, multiple layers are preferred. The multiple layers of the composition are preferably applied to the at least one surface of the medical device by repeating the steps discussed above. Preferably, the medical device is contacted with the composition three times, allowing the composition to dry on at least one surface of the medical device prior to contacting the medical device with the composition for each subsequent layer. In other words, the medical device preferably includes three coats, or layers, of the composition on at least one surface of the medical device.

In another embodiment, the method for coating medical devices with a composition coating includes the steps of forming a composition coating of an effective concentration to substantially prevent the growth or proliferation of biofilm on at least one surface of the medical device by dissolving the active components in an organic solvent, combining a medical device material penetrating agent to the active components and organic solvent, and combining an alkalinizing agent to improve the reactivity of the material of the medical device. The composition is then heated to a temperature ranging from about 30° C. to about 70° C. to enhance the adherence of the composition coating to at least one surface of the device. The composition coating is applied to at least one surface of the medical device, preferably by contacting the composition coating to the at least one surface of the medical device for a sufficient period of time for the composition coating to adhere to at least one surface of the medical device. The medical device is removed from the composition coating and allowed to dry for at least 8 hours, and preferably, overnight, at room temperature. The medical device may then be rinsed with a liquid, such as water and allowed to dry for at least 2 hours, and preferably 4 hours, before being sterilized. To facilitate drying of the composition of the invention onto the surface of the medical device, the medical device may be placed into a heated environment such as an oven.

In another embodiment, the method for coating the medical devices with a composition includes the steps of forming the composition and incorporating the composition into the material forming the medical device during the formation of the medical device. For example, the composition may be combined with the material forming the medical device, e.g., silicone, polyurethane, polyethylene, Gortex (polytetrafluoroethylene), Dacron™ (polyethylene tetraphthalate), Teflon™ (polytetrafluoroethylene), and/or polypropylene, and extruded with the material forming the medical device, thereby incorporating the composition into material forming the medical device. In this embodiment, the composition may be incorporated in a septum or adhesive which is placed at the medical device insertion or implantation site. An example of a coated medical device having a composition incorporated into the material forming the medical device in accordance with this embodiment is the catheter insertion seal having an adhesive layer described below in greater detail.

In still another aspect, the invention is directed to coated medical devices. Broadly, the coated medical devices include a composition coating applied to at least one surface of the medical device. Suitable medical devices and compositions are described above in greater detail. The composition may be applied to at least one surface of the medical devices in any suitable manner. For example, the composition may be applied to the medical devices following any of the methods described above in greater detail.

EXAMPLE 1

Effects of Ovotransferrin (OT), Protamine Sulfate (PS) and EDTA Alone and in Combinations on Biofilm Formation in Catheter-associated Bacteria Catheter-associated bacterial strains used: *E. coli* P18, *Proteus mirabilis*, *Pseudomonas aeruginosa*, *Klebsiella pneumoniae*, *Enterococcus faecalis* and *Staphylococcus epidermidis*

Method:

Base Formulas for Ovotranferrin (OT), Protamine Sulfate (PS) and EDTA were prepared as described in Table 1 below.

TABLE 1

| | Base Formulas for Screening (µg/ml of sterile water) | | | | |
| --- | --- | --- | --- | --- | --- |
| Compound | A | B | C | D | E |
| OT + PS | 125 + 12.5 | 250 + 25 | 500 + 50 | 1000 + 100 | 2000 + 200 |
| OT + EDTA | 125 + 12.5 | 250 + 25 | 500 + 50 | 1000 + 100 | 2000 + 200 |
| PS + EDTA | 12.5 + 12.5 | 25 + 25 | 50 + 50 | 100 + 100 | 200 + 200 |
| OT + PS + EDTA | 125 + 12.5 + 12.5 | 250 + 25 + 25 | 500 + 50 + 50 | 1000 + 100 + 100 | 2000 + 200 + 200 |

Studies were done to test biofilm formation in microtiter plate wells. Quantitative biofilm assay for catheter-associated bacteria was standardized following the procedure described by Jackson, et al. (J. Bacteriol. 184: 290-301). Bacteria were routinely cultured at 37° C. in Luria-Bertani (LB) or Tryptic Soy Broth (TSB). Biofilm assays were generally carried out in colony-forming antigen (CFA) medium at 26° C. However, biofilm assays for *Enterococcus faecalis* and *Staphylococcus epidermidis* were carried out in TSB at 37° C.

Overnight cultures were inoculated 5:100 into fresh medium. In the microtiter plate assay, inoculated cultures were grown in a 96-well polystyrene microtiter plate. Aqueous solutions of three compounds ovotransferrin, protamine sulfate and EDTA were prepared separately and appropriate volume of each one was added to microtiter plate wells in replicates individually and in combinations. Concentrations of three compounds, ovotransferrin, protamine sulfate and EDTA ranged from 0-2000 µg/ml and 0-200 µg/ml and 0-200 µg/ml, respectively. Growth of planktonic cells was determined by absorbance at 600 nm using Labsystems Multiskan Ascent microplate reader. Biofilm was measured by discarding the medium, rinsing the wells with water (three times) and staining bound cells with crystal violet. The dye was solubilized with 33% acetic acid, and absorbance at 630 nm was determined using a microtiter plate reader. For each experiment, background staining was corrected by subtracting the crystal violet bound to uninoculated control.

Results:

FIGS. 1-12 show biofilm formation by the above catheter-associated bacterial strains in the wells of microtiter plate in the presence and absence of ovotransferrin, protamine sulfate and EDTA alone and in combinations at different concentrations. Values represent the Mean±Standard Deviation of three experiments with four replicates for each concentration. The composition consisting of all three compounds showed synergistic inhibitory effects on biofilm formation in *Pseudomonas aeruginosa, Klebsiella pneumoniae* and *Staphylococcus epidermidis* (FIGS. 7-12). Furthermore, ovotransferrin and protamine sulfate together also showed synergistic inhibitory effects on biofilm formation in *Proteus mirabilis, Klebsiella pneumoniae, Staphylococcus epidermidis* and *Pseudomonas aeruginosa* (FIGS. 1-6).

EXAMPLE 2

Effects of Synergistic Composition on Biofilm Formation by Catheter-associated Bacteria in Urinary Catheter Catheter-associated bacterial strains used: *E. coli* P18, *Proteus mirabilis, Pseudomonas aeruginosa, Klebsiella pneumoniae, Enterococcus faecalis* and *Staphylococcus epidermidis*

Method:

To visualize biofilm formation in catheters, 35 µl of an overnight culture of each of the above bacterial strain was inoculated into 700 µl of medium and injected into clear vinyl urethral catheters overnight at 26 or 37° C. with and without composition consisting of 1000 µg ovotransferrin/ml +100 µg protamine sulfate/ml+100 µg EDTA/ml. The catheters were capped at both ends. The media and growth conditions were as described above for microtiter plate assay. Cultures were removed to determine the growth at 600 nm and the catheters were rinsed with distilled water. After drying at room temperature for 15 min., 700 µl of 1% crystal violet was added to the catheters for 20 min. The stained biofilms were rinsed several times with distilled water, and allowed to dry at room temperature for 15 min before examination. The dye was solubilized with 33% acetic acid, and absorbance at 630 nm was determined using a spectrophotometer. The effect of composition on biofilm formation by catheter-associated bacterial strains such as *Staphylococcus epidermidis, Proteus mirabilis* and *Pseudomonas aeruginosa* was tested by growth of the organisms in urethral catheters as described above.

Figure 13:
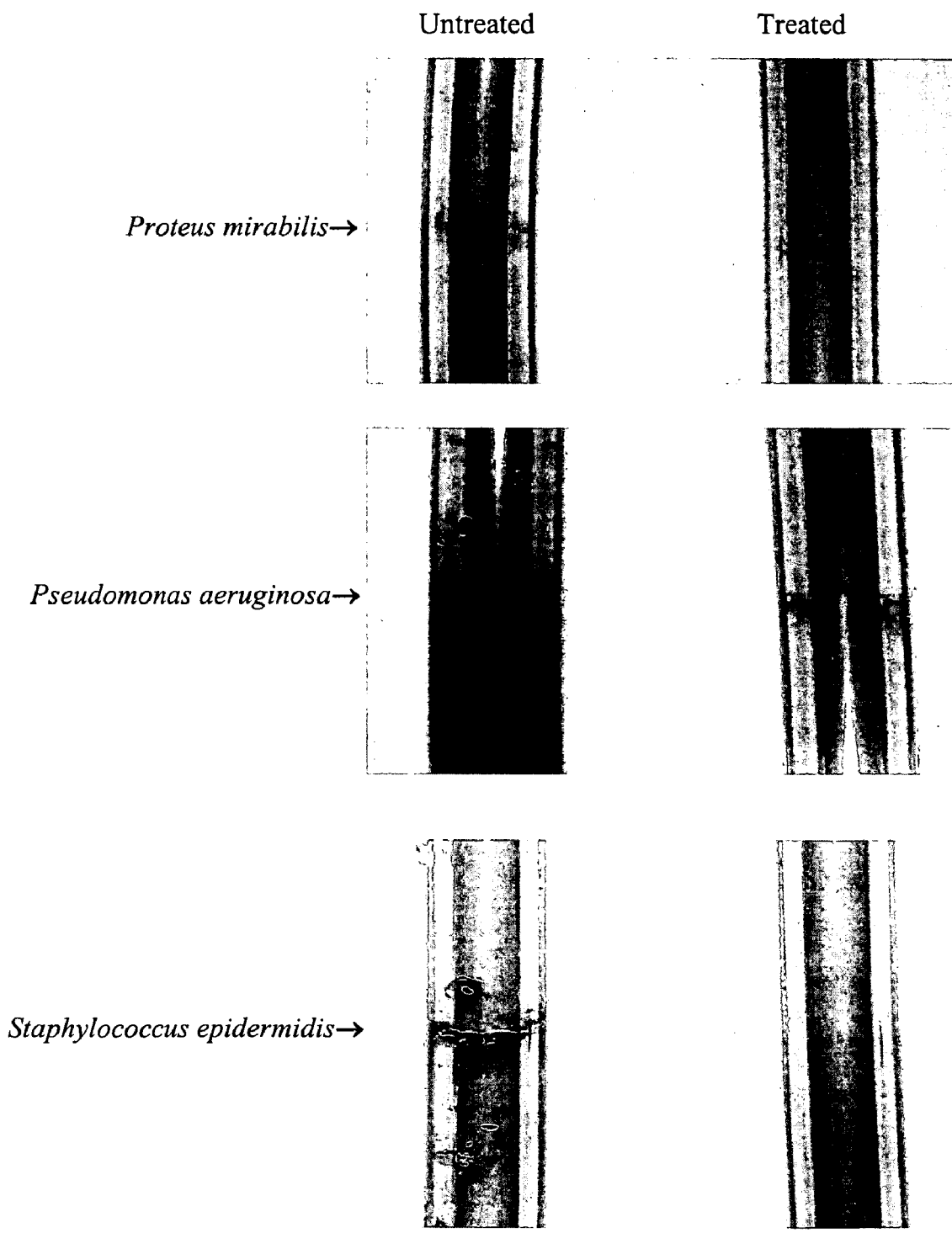
FIG. 13 shows the effects of synergistic composition on biofilm formation by *Proteus mirabilis, Pseudomonas aeruginosa* and *Staphylococcus epidermidis* in a catheter.

Results:

*Staphylococcus epidermidis* and *Proteus mirabilis* formed biofilms mainly at the air liquid interface, while the biofilm formed by *Pseudomonas aeruginosa* was dispersed all along the catheter. The composition inhibited biofilm formation in all organisms (FIG. 13, Table 2).

TABLE 2

Biofilm formation by catheter-associated bacteria in urinary catheters treated with synergistic antimicrobial composition*

| Organism | Treated (OD) | Untreated (OD) | Inhibition (%) |
| --- | --- | --- | --- |
| *Proteus mirabilis* | 0.0 | 0.10 | 100 |
| *Pseudomonas aeruginosa* | 0.20 | 0.96 | 79 |
| *Staphylococcus epidermidis* | 0.01 | 0.20 | 95 |

*Optical Density (OD) readings are based on crystal violet staining

EXAMPLE 3

Effect of Synergistic Composition on the Viable Cell Counts of Catheter-associated Bacteria Catheter-associated bacterial strains used: *E. coli* P18, *Proteus mirabilis, Pseudomonas aeruginosa, Klebsiella pneumoniae, Enterococcus faecalis* and *Staphylococcus epidermidis*

Method:

Viable cell counts of catheter-associated bacterial strains were determined following a standard serial dilution plating method. The cultures of all six bacterial strains were grown in the presence and absence of a synergistic antimicrobial composition (OT+PS+EDTA=1000+100+100 µg/ml) using CFA medium (for gram-negative strains) and TSB (for gram-positive strains) at 26° C. and 37° C., respectively for 24 hours and serially diluted (10-fold dilution) with sterile water. The number of dilutions depended on the initial density of the cell suspension. Plated out 100 µl of each dilution on LB agar or Tryptic Soy agar plates in duplicates. The aliquot over the agar plate surface was spread with a sterile plastic spreader. The plates were incubated overnight at 37° C. and colony-forming units (CFU) were counted and converted to original numbers/ml (CFU/ml) of suspension. Further, viable cell counts of treated cultures were compared with that of untreated ones (Table 3).

Results:

While the synergistic composition had dramatic effect on the viable cell counts of *E. coli* and *Staphylococcus epidermidis*, it hardly showed any effect on that of other test organisms. Interestingly, when planktonic growth was measured in terms of turbidity on microtiter-plate the synergistic composition appeared to have minimal effect on the growth as compared to its effect on biofilm formation in all test organisms (see Example 1).

TABLE 3

Effect of synergistic composition on the viable cell counts of catheter-associated bacteria

| Organism | Treated (CFU/ml) | Untreated (CFU/ml) | % Reduction |
|---|---|---|---|
| Escherichia coli P18 | $8.2 \times 10^7$ | $4.6 \times 10^{12}$ | 99.99 |
| Proteus mirabilis | $2.4 \times 10^{14}$ | $8.4 \times 10^{13}$ | 0.0 |
| Klebsiella pneumoniae | $7.1 \times 10^{19}$ | $3.2 \times 10^{18}$ | 0.0 |
| Pseudomonas aeruginosa | ND | ND | ND |
| Enterococcus mirabilis | $1.6 \times 10^{15}$ | $6.4 \times 10^{14}$ | 0.0 |
| Staphylococcus epidermidis | $1.0 \times 10^6$ | $1.6 \times 10^9$ | 99.93 |

ND = Not Determined

EXAMPLE 4

Effect of Coating Urinary Catheter with Tridodecyl Methyl Ammonium Chloride (TDMAC) Plus Synergistic Antimicrobial Composition on the Growth of Catheter-associated Bacteria Catheter-associated bacterial strains used: *Pseudomonas aeruginosa, Klebsiella pneumoniae* and *Staphylococcus epidermidis*

Method:

Clear vinyl catheter segments (3 cm sections of tubing) that had been preheated (incubated in sterile water at 65° C. overnight) were coated in 5% TDMAC in ethanol for an hour at room temperature. The catheter segments were vigorously washed with sterile water and air-dried. The segments were then immersed in ethanol and coating solution (1000 μg OT+100 μg PS+100 μg EDTA/ml of water) for 2 hours at −20° C. In addition, a few catheter segments were immersed in coating solution alone for 2 hours at −20° C. All the segments were air dried and immersed in a tryptic soy broth culture of *Pseudomonas aeruginosa, Klebsiella pneumoniae* and *Staphylococcus epidermidis* for 3 hours at 37° C. The catheter segments were washed 3 times in 3 changes of sterile saline and rolled on tryptic soy agar plates. The plates were incubated overnight at 37° C. and the colonies were counted. Proper controls were used as shown in the Table 4.

Results: See Table 4

TABLE 4

Effect of coating urinary catheter with TDMAC plus synergistic antimicrobial composition on the growth of catheter-associated bacteria

| Bacterial Strain & Coating | Viable Counts (CFU/mM)* | % Inhibition |
|---|---|---|
| *Staph. epidermidis* | | |
| Control (uncoated) | 16.8 ± 3.3 | 0 |
| Composition | 13.2 ± 0.6 | 21 |
| TDMAC | 20.4 ± 7.7 | 0 |
| TDMAC + Composition | 11.0 ± 1.3 | 35 |
| *Klebsiella pneumoniae* | | |
| Control (uncoated) | 3.8 ± 0.9 | 0 |
| Composition | 2.3 ± 1.8 | 40 |
| TDMAC | 4.3 ± 1.3 | 0 |
| TDMAC + Composition | 1.6 ± 0.6 | 59 |

TABLE 4-continued

Effect of coating urinary catheter with TDMAC plus synergistic antimicrobial composition on the growth of catheter-associated bacteria

| Bacterial Strain & Coating | Viable Counts (CFU/mM)* | % Inhibition |
|---|---|---|
| *Pseudomonas aeruginosa* | | |
| Control (uncoated) | 21.2 ± 1.5 | 0 |
| Composition | 15.3 ± 1.3 | 28 |
| TDMAC | 18.8 ± 4.6 | 12 |
| TDMAC + Composition | 9.8 ± 0.5 | 54 |

*Colony Forming Units (CFU) per millimeter of catheter tubing

EXAMPLE 5

Effect of Coating Urinary Catheter with Polyvinylpyrrolidone (PVP) Hydrogel Plus Synergistic Antimicrobial Composition on the Growth of Catheter-associated Bacteria Catheter-associated bacterial strains used: *Pseudomonas aeruginosa, Klebsiella pneumoniae* and *Staphylococcus epidermidis*

Method:

Clear vinyl catheter segments (3 cm sections of tubing) that had been preheated (incubated in sterile water at 65° C. overnight) were immersed in PVP-hydrogel (10% PVP) and coating solution (1000 μg OT+100 μg PS+100 μg EDTA/ml of water) for 2 hours at 37° C. In addition, a few segments were immersed in coating solution alone for 2 hours at 37° C. All the catheter segments were air dried and immersed in a tryptic soy broth culture of *Pseudomonas aeruginosa, Klebsiella pneumoniae* and *Staphylococcus epidermidis* for 3 hours at 37° C. The catheter segments were washed 3 times in 3 changes of sterile saline and rolled on tryptic soy agar plates. The plates were incubated overnight at 37° C. and the colonies were counted. Proper controls were used as shown in the Table 5.

Results: See Table 5

TABLE 5

Effect of coating urinary catheter with PVP-Hydrogel plus synergistic antimicrobial composition on the growth of catheter-associated bacteria

| Bacterial Strain & Coating | Viable Counts (CFU/mM)* | % Inhibition |
|---|---|---|
| *Staph. epidermidis* | | |
| Control (uncoated) | 6.3 ± 0.7 | 0 |
| Composition | 5.4 ± 2.3 | 14 |
| PVP-Hydrogel | 5.8 ± 1.1 | 8 |
| PVP-Hydrogel + Composition | 1.8 ± 1.1 | 60 |
| *Klebsiella pneumoniae* | | |
| Control (uncoated) | 3.6 ± 2.4 | 0 |
| Composition | 1.6 ± 0.2 | 57 |
| PVP-Hydrogel | 1.5 ± 0.6 | 59 |
| PVP-Hydrogel + Composition | 0.4 ± 0.1 | 88 |
| *Pseudomonas aeruginosa* | | |
| Control (uncoated) | 9.6 ± 2.5 | 0 |
| Composition | 6.6 ± 0.9 | 32 |
| PVP-Hydrogel | 8.2 ± 2.3 | 15 |
| PVP-Hydrogel + Composition | 3.2 ± 1.7 | 67 |

*Colony Forming Units (CFU) per millimeter of catheter tubing

Numerous modifications and variations of practicing the present invention are possible in light of the above teachings and therefore fall within the scope of the following claims.

REFERENCES

Bezkorovainy, "Antimicrobial properties of iron-binding proteins", Adv. Exp. Med. Biol., 135:139-154, 1981

Costerton, et al., "Bacterial Biofilms: A common cause of persistent infections", Science, 284:1318-1322, 1999

Darouiche, et al., "Antimicrobial activity and durability of a novel antimicrobial-impregnated bladder catheter", Int. J. Antimicrob. Ag., 8:243-247, 1997

Darouiche, et al., "A comparison of two antimicrobial-impregnated central venous catheters", New. Eng. J. Med., 340:1-8, 1999

Donlan, "Biofilms and device-associated infections", Emerging Infectious Diseases, 7:277-281, 2001

Fallgren, et al., "In vitro anti-Staphylococcal activity of heparinized biomaterials bonded with combinations of rifampin", Zent. Fur Bakt.-Int. J. Med. Micro. Vir. Paraotol. Infect. Dis., 287:19-31, 1998

Jackson, et al., "Biofilm formation and dispersal under the influence of the global regulator CsrA of *Escherichia coli*", J. Bacteriol., 184:290-301, 2002

Johnson, et al., "Activities of a nitrofurazone-containing urinary catheters and a silver hydrogel catheter against multidrug resistant bacteria characteristic of catheter-associated urinary tract infection", Antimicrob. Agents Chemother., 43:2,990-2,995, 1999

Jones, et al., "Physicochemical characterization of hexetidine impregnated endotracheal tube poly (vinylchloride) and resistance to adherence of respiratory bacterial pathogens", Pharm. Res. (in press)

Maki and Tambyah, "Engineering out the risk of infection with urinary catheters", Emerging Infectious Diseases, 7:1-6, 2001

Raad, et al., "Minocycline and ethylenediaminetetraacetate for the prevention of recurrent vascular catheter infections", Clinical Infectious Diseases, 25:149-151, 1997

Raad, et al., "Antimicrobial durability and rare ultrastructural colonization of indwelling central catheters coated with minocycline and rifampin", Crit. Care. Med., 26:219-224, 1998

Schierholz, et al., "Controlled release of antibiotics from biomedical polyurethanes", Biomaterials, 18:839-844, 1997

Stickler, "Biomaterials to prevent nosocomial infections: Is silver the gold standard?", Curr. Opin. Infect. Dis., 13:389-393, 2000

Tunney, et al., "Infection associated with medical devices", Reviews in Medical Microbiology, 74:195-205, 1996.

I claim:

1. A medical device comprising a composition, wherein said composition comprises an effective amount of (a) ovotransferrin, protamine sulfate, and ethylenediaminetetraacetic acid (EDTA) or (b) ovotransferrin and protamine sulfate, wherein the effective amount of (a) or (b) inhibits formation of a bacterial biofilm.

2. The medical device of claim 1, wherein the medical device is selected from the group consisting of a tubing, a catheter, a pacemaker, a prosthetic heart valve, a prosthetic joint, a voice prosthetic device, a contact lens, a vascular graft, a vascular catheter port, a wound drain tube, a hydrocephalus shunt, a heart valve, a heart assist device, a pacemaker capsule, an incontinence device, a penile implant, a joint replacement, a cannula, an elastomer, a hydrogel, a surgical instrument, a dental instrument, a fabric, an adhesive, a bandage, an orthopedic implant, and an intrauterine device.

3. The medical device of claim 2, wherein the catheter is selected from the group consisting of a central venous catheter, a dialysis catheter, a long-term tunneled central venous catheter, a pulmonary artery Swan-Ganz catheter, a urinary catheter, a ventricular catheter, and a peritoneal catheter.

4. The medical device of claim 2, wherein the intrauterine device is selected from the group consisting of long term urinary devices, urinary dilators, and tissue bonding urinary devices.

5. The medical device of claim 2, wherein the tubing is selected from the group consisting of intravenous tube, breathing tube, dental water line, dental drain tube, and feeding tube.

6. An article for inhibiting formation of bacterial biofilm comprising a coating and a medical device wherein said coating comprises: an effective amount of (a) ovotransferrin, protamine sulfate, and ethylenediaminetetraacetic acid (EDTA) or (b) ovotransferrin and protamine sulfate, wherein the effective amount of (a) or (b) inhibits formation of a bacterial biofilm.

7. The article of claim 6, wherein the device comprises a material selected from the group consisting of silicone, polyurethane, polyethylene, polytetrafluoroetheylene, polyethylene tetraphthalate, polypropylene, and mixtures thereof.

8. The article of claim 6, wherein the medical device is selected from the group consisting of a tubing, a catheter, a pacemaker, a prosthetic heart valve, a prosthetic joint, a voice prosthetic device, a contact lens, a vascular graft, a vascular catheter port, a wound drain tube, a hydrocephalus shunt, a heart valve, a heart assist device, a pacemaker capsule, an incontinence device, a penile implant, a joint replacement, a cannula, an elastomer, a hydrogel, a surgical instrument, a dental instrument, a fabric, an adhesive, a bandage, an orthopedic implant, and an intrauterine device.

9. The article of claim 8, wherein the catheter is selected from the group consisting of a central venous catheter, a dialysis catheter, a long-term tunneled central venous catheter, a pulmonary artery Swan-Ganz catheter, a urinary catheter, a ventricular catheter, and a peritoneal catheter.

10. The article of claim 8, wherein the intrauterine device is selected from the group consisting of long term urinary devices, urinary dilators, and tissue bonding urinary devices.

11. The article of claim 8, wherein the tubing is selected from the group consisting of intravenous tube, breathing tube, dental water line, dental drain tube, and feeding tube.

* * * * *

UNITED STATES PATENT AND TRADEMARK OFFICE
CERTIFICATE OF CORRECTION

PATENT NO. : 7,314,857 B2
APPLICATION NO. : 10/781464
DATED : January 1, 2008
INVENTOR(S) : Madhyastha It is certified that error appears in the above-identified patent and that said Letters Patent is hereby corrected as shown below:

Col. 1, line 40: "kidney stone and host of nosocomial infections" should read --kidney stone and a host of nosocomial infections--

Col. 6, line 63: "to what which has been used in the fast) to be effective." should read --to what which has been used in the past) to be effective.--

Col. 9. lines 2 and 3: "Dacron$^{TM}$" should read --Dacron$^{®}$--

Col. 9, line 31: "polyvinylamine" should read --polyvinylarnine--

Col. 9, line 40: "Dacron$^{TM}$" should read --Dacron$^{®}$--

Col. 9, line 41: "Dacron" should read --Dacron$^{®}$--

Col. 11, lines 19-20: "25°C." should read --25°C--

Col. 11, line 49: "a temperature ranging from about 30°C. to about 70°C. to" should read --a temperature ranging from about 30°C to about 70°C to--

Col. 12, line 17: "Dacron$^{TM}$" should read --Dacron$^{®}$--

Col. 12, line 18: "Teflon$^{TM}$" should read --Teflon$^{®}$--

Col. 13, line 2: "37°C." should read --37°C--

Col. 13, line 58: "37°C." should read --37°C--

Col. 14, line 47: "26°C. and 37°C.," should read --26°C and 37°C,--

Col. 14, line 54: "37°C." should read --37°C--

UNITED STATES PATENT AND TRADEMARK OFFICE
CERTIFICATE OF CORRECTION

| | |
|---|---|
| PATENT NO. | : 7,314,857 B2 |
| APPLICATION NO. | : 10/781464 |
| DATED | : January 1, 2008 |
| INVENTOR(S) | : Madhyastha |

It is certified that error appears in the above-identified patent and that said Letters Patent is hereby corrected as shown below:

Col. 15, line 33: "65°C." should read --55°C--

Col. 15, line 46: "37°C." should read --37°C--

Col. 16, line 29: "65°C." should read --65°C--

Col. 16, line 39: "37°C." should read --37°C--

Col. 18, line 6: "implant, a joint replacement, a cannula, an elastorner, a" should read --implant, a joint replacement, a cannula, an elastomer, a--

Signed and Sealed this

Fifteenth Day of July, 2008

JON W. DUDAS
*Director of the United States Patent and Trademark Office*